(12) United States Patent
Stewart

(10) Patent No.: US 6,264,646 B1
(45) Date of Patent: Jul. 24, 2001

(54) METHOD FOR PREVENTING AND REVERSING ATHEROSCLEROSIS IN MAMMALS

(75) Inventor: Duncan J. Stewart, Toronto (CA)

(73) Assignee: Vasogen Ireland Limited, Shannon (IE)

(*) Notice: Subject to any disclaimer, the term of this patent is extended or adjusted under 35 U.S.C. 154(b) by 0 days.

(21) Appl. No.: 09/304,262

(22) Filed: May 6, 1999

Related U.S. Application Data

(63) Continuation-in-part of application No. 09/190,236, filed on Nov. 13, 1998.

(51) Int. Cl.[7] .................................................. A61M 31/00
(52) U.S. Cl. .......................... 604/522; 128/898; 250/432; 250/435; 250/504; 604/500
(58) Field of Search ............................. 128/898; 604/500, 604/522; 250/432, 435, 504

(56) References Cited

U.S. PATENT DOCUMENTS

| | | |
|---|---|---|
| 4,831,268 | 5/1989 | Fisch et al. . |
| 4,968,483 | 11/1990 | Müller et al. . |
| 5,591,457 | 1/1997 | Bolton . |
| 5,834,030 | 11/1998 | Bolton . |

FOREIGN PATENT DOCUMENTS

| | | |
|---|---|---|
| 2194485 | 11/1996 | (CA) . |
| 1 068 428 | 11/1959 | (DE) . |
| WO 93/15778 | 8/1993 | (WO) . |
| WO 98/07436 | 2/1998 | (WO) . |

*Primary Examiner*—David J. Isabella
*Assistant Examiner*—Kelly O'Hara
(74) *Attorney, Agent, or Firm*—Burns, Doane, Swecker & Mathis, LLP

(57) ABSTRACT

A method for delaying the onset, retarding the progression, and causing regression of atherosclerosis in a mammal comprises: (a) treating an aliquot of mammalian blood ex vivo with at least one stressor selected from the group consisting of a temperature above or below body temperature, ultraviolet light and an oxidative environment; and (b) administering the aliquot of blood treated in step (a) to the mammal, wherein the aliquot has a volume sufficient to achieve a reduction in lipid levels in the mammal.

22 Claims, 1 Drawing Sheet

(1 of 1 Drawing Sheet(s) Filed in Color)

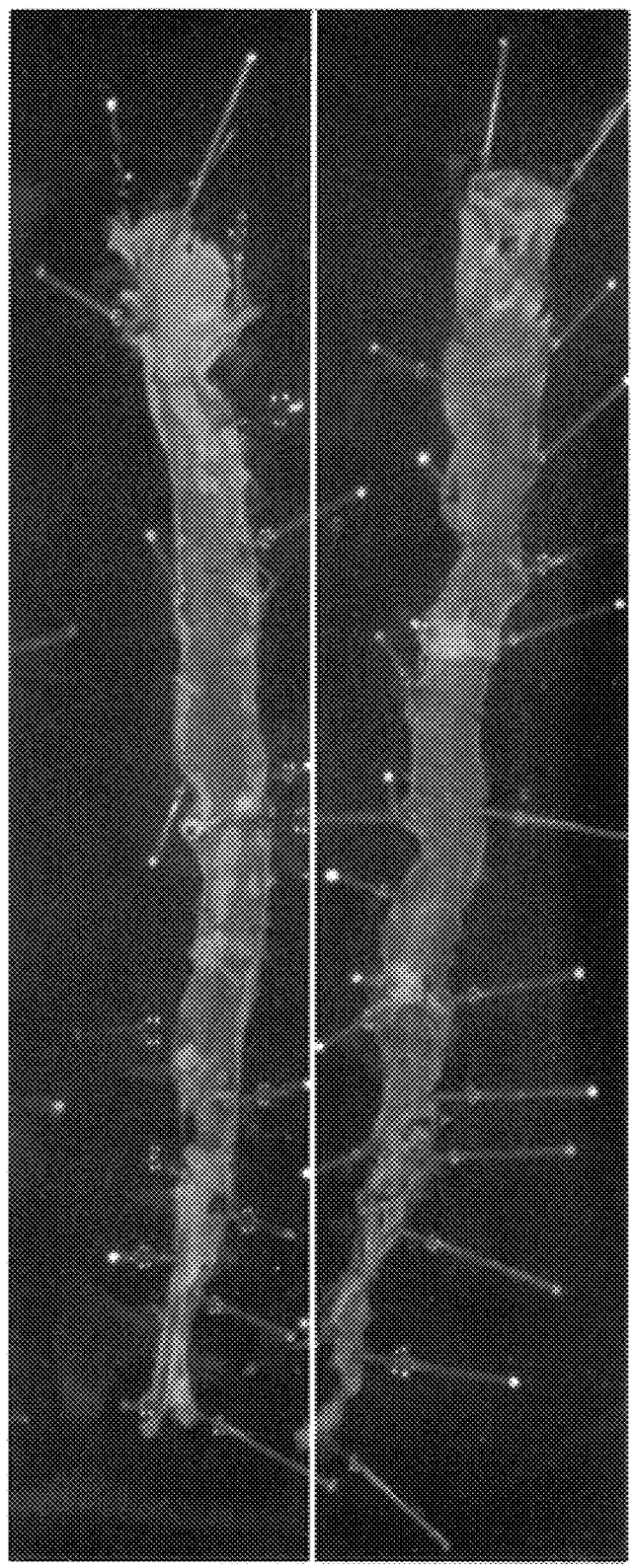
FIG._1A  FIG._1B

METHOD FOR PREVENTING AND REVERSING ATHEROSCLEROSIS IN MAMMALS

This application is a continuation-in-part application of U.S. patent application Ser. No. 09/190,236 filed Nov. 13, 1998.

FIELD OF THE INVENTION

This invention relates to treatment of blood, and to the use of treated, modified blood in connection with certain abnormal mammalian physical conditions and disease states. More specifically, it relates to modified mammalian blood and the treatment of cardiovascular disorders associated with elevated levels of lipids in the blood, in a mammalian subject, by administration to the subject of such modified blood.

BACKGROUND OF THE INVENTION

Hyperlipidemias such as hypercholesterolemia and elevated serum triglyceride levels are among the most potent risk factors in the causation of atherosclerosis, which is the build-up of fatty plaque deposits within the walls of blood vessels. For example, nigh levels of serum cholesterol bound to low density lipoprotein (LDL), intermediate density lipoprotein (IDL) or very low density lipoprotein (VLDL) are known to correlate strongly with the occurrence of atherosclerosis in humans. In particular, it is believed that the higher the circulating levels of cholesterol in the form of LDL, IDL and VLDL cholesterol, and the higher the circulating levels of other lipids such as triglycerides, the more likely it is that cholesterol and lipids will be deposited within the blood vessel wall and cause or contribute to atherosclerosis In hypercholesterolemia, for example, the increase in the blood cholesterol level is associated mainly with a rise in the concentration of LDL, IDL and VLDL cholesterol. However, the specific causes of hypercholesterolemia are complicated and varied. At least one kind of hypercholesterolemia, known as familial hypercholesterolemia, is caused by a mutation in the gene for the LDL receptor that moves cholesterol out of the blood, primarily in the liver. Much more commonly, hypercholesterolemia has been associated with high dietary intake of saturated fatty acids and cholesterol, resulting in elevated blood cholesterol levels. High serum triglyceride levels have also been associated with high dietary intake of fatty acids.

Reduction of hyperlipidemia, including hypercholesterolemia, results in a delayed onset of atherosclerosis and a decrease in the progression of atherosclerosis, thus reducing the risk of coronary heart disease. In addition, there is evidence that relatively complicated plaques induced by hyperlipidemia can regress, and that further progression of atherosclerosis will decrease or cease when hyperlipidemia is removed. Some forms of hyperlipidemia, including hypercholesterolemia, are potentially partially reversible with current techniques of preventive management. Taking cholesterol-lowering drugs can result in a reduction in serum cholesterol, and other drugs may lower serum triglyceride levels. However, drugs are not always warranted for hyperlipidemia, and some lipid-lowering drugs may have serious side effects. Dietary therapy is usually recommended for all patients with hyperlipidemia but the effect is often not sufficient to reduce risk optimally.

Therefore, there is a need for a method which is effective in lowering blood lipid levels, especially cholesterol and triglyceride levels, and which does not have significant side effects.

SUMMARY OF THE INVENTION

The present invention overcomes at least some of the above-noted and other disadvantages of presently known therapies for treatment of hyperlipidemia, such as hypercholesterolemia and elevated serum triglyceride levels, by providing a method for treating hyperlipidemia in which an aliquot of mammalian blood is treated ex vivo and subsequently introduced into the body of a mammalian subject.

The aliquot of blood is treated by being subjected to one or more stressors which have been found to modify the blood. According to the present invention, the blood aliquot can be modified by subjecting the blood, or separated cellular or non-cellular fractions of the blood, or mixtures of the separated cells and/or non-cellular fractions of the blood, to stressors selected from heat, ultraviolet light and oxidative environments such as treatment with ozone/oxygen mixtures, or any combination of such stressors, simultaneously or sequentially.

The observed effects of the modified blood of the present invention, when introduced into the mammalian subject's body, are several in number. Firstly, there is an observed reduction in total serum cholesterol levels, primarily due to a reduction in the levels of LDL and VLDL cholesterol. Levels of beneficial HDL cholesterol are not reduced. Reductions in cholesterol levels of as high as about 40 percent, as compared to subjects which received untreated blood as a placebo, have been observed. Secondly, there is an observed reduction in serum triglyceride levels. Such reductions in serum cholesterol and triglycerides would be expected to delay the onset and retard the progression of atherosclerosis due to hyperlipidemia.

Another of the observed effects of the treatment according to the present invention is that mammalian subjects treated according to the present invention show substantially reduced deposition of lipids within blood vessel walls, as compared to untreated subjects. As well as retarding the progression of plaque deposition, the treatment of the invention has been shown to cause existing plaques to regress. It is believed that this observed vessel protection is due at least in part to the reduced serum lipid levels in subjects treated by the method of the present invention. However, the reduced deposition of lipids within blood vessel walls has also been observed in the absence of a reduction in serum lipids.

Accordingly, in one aspect the present invention provides a method of reducing the serum level of a lipid in a mammal, comprising; (a) treating an aliquot of mammalian blood ex vivo with at least one stressor selected from the group consisting of a temperature above or below body temperature, ultraviolet light and an oxidative environment; and (b) administering the aliquot of blood treated in step (a) to the mammal, wherein the aliquot has a volume sufficient to achieve a reduction in the serum lipid level in the mammal.

In another aspect, the present invention provides a method of preventing or treating a condition in a mammalian subject, said method reducing the serum level of a lipid in the mammal and comprising (a) treating an aliquot of mammalian blood ex vivo with at least one stressor selected from the group consisting of a temperature above or below body temperature, ultraviolet light and an oxidative environment; and (b) administering the aliquot of blood treated in step (a) to the mammal, wherein the aliquot has a volume sufficient to achieve a reduction in the serum lipid level in the mammal.

BRIEF DESCRIPTION OF THE DRAWINGS

The file of this patent contains at least one drawing executed in color. Copies of this patent with color drawing (s) will be provided by the Patent and Trademark Office upon request and payment of the necessary fee.

The invention will now be more fully described, by way of example only, with reference to the accompanying drawings, in which.

FIG. 1 is a photograph showing two fall length aortae obtained from LDL receptor deficient mice which underwent the study described in Example 1, the aorta labeled "A" being obtained from an animal which received a high cholesterol diet and sham treatments, and the aorta labeled "B" being obtained from an animal which received a high cholesterol diet and was treated according to a preferred method of the present invention, with aortic lipid deposition being made visible by staining the aortae with oil red O. FIG. 1 is identical to FIG. 1 of co-pending application no. 09/190,236, of which this application is a continuation-in-part, and which is incorporated herein by reference.

DETAILED DESCRIPTION OF PREFERRED EMBODIMENTS

According to a preferred process of the present invention, an aliquot of blood is extracted from a mammalian subject, preferably a human, and the aliquot of blood is treated ex vivo with certain stressors, described in more detail below. The terms "aliquot", "aliquot of blood" or similar terms used herein include whole blood, separated cellular fractions of the blood including platelets, separated non-cellular fractions of the blood including plasma, and combinations thereof The effect of the stressors is to modify the blood, and/or the cellular or non-cellular fractions thereof, contained in the aliquot. The modified aliquot is then re-introduced into the subject's body by any method suitable for vaccination, preferably selected from intra-arterial injection, intramuscular injection, intravenous injection, subcutaneous injection, intraperitoneal injection, and oral, nasal or rectal administration.

The stressors to which the aliquot of blood is subjected ex vivo according to the method of the present invention are selected from temperature stress (blood temperature above or below body temperature), an oxidative environment and ultraviolet light, individually or in any combination, simultaneously or sequentially. Suitably, in human subjects, the aliquot has a volume sufficient that, when re-introduced into the subject's body, a reduction in a serum lipid level and/or a retardation in progression or a regression of atherosclerotic plaque formation is achieved in the subject. Preferably, the volume of the aliquot is up to about 400 ml, preferably from about 0.1 to about 100 ml, more preferably from about 5 to about 15 ml, even more preferably from about 8 to about 12 ml, and most preferably about 10 ml.

It is preferred, according to the invention, to apply all three of the aforementioned stressors simultaneously to the aliquot under treatment, in order to ensure the appropriate modification to the blood. It may also be preferred in some embodiments of the invention to apply any two of the above stressors, for example to apply temperature stress and oxidative stress, temperature stress and ultraviolet light, or ultraviolet light and oxidative stress. Care must be taken to utilize an appropriate level of the stressors to thereby effectively modify the blood to achieve a serum lipid reduction in the subject.

The temperature stressor warms the aliquot being treated to a temperature above normal body temperature or cools the aliquot below normal body temperature. The temperature is selected so that the temperature stressor does not cause excessive hemolysis in the blood contained in the aliquot and so that, when the treated aliquot is injected into a subject, a lipid reduction and/or a retardation in progression or regression in the formation of atherosclerotic plaque will be achieved. Preferably, the temperature stressor is applied so that the temperature of all or a part of the aliquot is up to about 55° C., and more preferably in the range of from about −5° C. to about 55° C.

In some preferred embodiments of the invention, the temperature of the aliquot is raised above normal body temperature, such that the mean temperature of the aliquot does not exceed a temperature of about 55° C., more preferably from about 40° C. to about 50° C., even more preferably from about 40° C. to about 44° C., and most preferably about 42.5±1° C.

In other preferred embodiments: the aliquot is cooled below normal body temperature such that the mean temperature of the aliquot is within the range of from about −5° C. to about 36.5° C., even more preferably from about 10° C. to about 30° C., and even more preferably from is about 15° C. to about 25° C.

The oxidative environment stressor can be the application to the aliquot of solid, liquid or gaseous oxidizing agents. Preferably, it involves exposing the aliquot to a mixture of medical grade oxygen and ozone gas, most preferably by bubbling through the aliquot, at the aforementioned temperature range, a stream of medical grade oxygen gas having ozone as a minor component therein. The ozone content of the gas stream and the flow rate of the gas stream are preferably selected such that the amount of ozone introduced to the blood aliquot, either on its own or in combination with other stressors, does not give rise to excessive levels of cell damage such that the therapy is rendered ineffective. Suitably, the gas stream has an ozone content of up to about 300 $\mu$g/ml, preferably up to about 100 $\mu$g/ml, more preferably about 30 $\mu$g/ml, even more preferably up to about 20 $\mu$g/ml, particularly preferably from about 10 $\mu$g/ml to about 20 $\mu$g/ml, and most preferably about 14.5±1.0 $\mu$g/ml. The gas stream is suitably supplied to the aliquot at a rate of up to about 2.0 liters/min, preferably up to about 0.5 liters/min, more preferably up to about 0.4 liters/min, even more preferably up to about 0.33 liters/min, and most preferably about 0.24±0.024 liters/min. The lower limit of the flow rate of the gas stream is preferably not lower than 0.01 liters/min, more preferably not lower than 0.1 liters/min, and even more preferably not lower than 0.2 liters/min.

The ultraviolet light stressor is suitably applied by irradiating the aliquot under treatment from a source of UV light while the aliquot is maintained at the aforementioned temperature and while the oxygen/ozone gaseous mixture is being bubbled through the aliquot. Preferred UV sources are UV lamps emitting UV-C band wavelengths, i.e. at wavelengths shorter than about 280 nm. Ultraviolet light corresponding to standard LTV-A (wavelengths from about 315 to about 400 nm) and UV-B (wavelengths from about 280 to about 315) sources can also be used. For example, an appropriate dosage of such UV light, applied simultaneously with the aforementioned temperature and oxidative environment stressors, can be obtained from up to eight lamps arranged to surround the sample container holding the aliquot, operated at an intensity to deliver a total UV light energy at the surface of the blood of from about 0.025 to about 10 joules/cm$^2$, preferably from about 0.1 to about 3.0 joules/cm$^2$, may advantageously be used. Preferably, four such lamps are used.

The time for which the aliquot is subjected to the stressors is normally within the time range of up to about 60 minutes.

The time depends to some extent upon the chosen intensity of the UV light, the temperature, the concentration of the oxidizing agent and the rate at which it is supplied to the aliquot. Some experimentation to establish optimum times may be necessary on the part of the operator, once the other stressor levels have been set. Under most stressor conditions, preferred times will be in the approximate range of from about 2 to about 5 minutes, more preferably about 3 minutes. The starting blood temperature, and the rate at which it can be warmed or cooled to a predetermined temperature, tends to vary from subject to subject. Such a treatment provides a modified blood aliquot which is ready for injection into the subject.

In the practice of the preferred process of the present invention, the blood aliquot may be treated with the stressors using an apparatus of the type described in U.S. Pat. No. 4,968,483 to Mueller. The aliquot is placed in a suitable, sterile, UV light-transmissive container, which is fitted into the machine. The UV lamps are switched on for a fixed period before the gas flow is applied to the aliquot providing the oxidative stress, to allow the output of the UV lamps to stabilize. The UV lamps are typically on while the temperature of the aliquot is adjusted to the predetermined value, e.g. 42.5±1° C. Then the oxygen/ozone gas mixture, of known composition and controlled flow rate, is applied to the aliquot, for the predetermined duration of up to about 60 minutes, preferably 2 to 5 minutes and most preferably about 3 minutes as discussed above, so that the aliquot experiences all three stressors simultaneously. In this way, blood is appropriately modified according to the present invention to achieve the desired effects.

The invention is further illustrated and described with reference to the following specific examples.

EXAMPLE 1

Animal Studies

Model

The purpose of the experiment is to determine the effects of treatment according the present invention on the development of atherosclerosis in the LDL receptor (LDL-R) deficient mouse model, a widely used transgenic atherosclerosis model created by targeted disruption of the LDL receptor. This animal model is analogous to familial hypercholesterolemia, an inherited condition in which a mutation results in complete lack of functional LDL-R. In the human disease, homozygous individuals demonstrate a marked increase in serum cholesterol and develop severe premature atherosclerosis, often succumbing to this disease at an early age. In patients with this disease, currently used lipid lowering agents do not have a significant effect in terms of lowering cholesterol levels.

The LDL-R deficient mouse model shows intolerance to cholesterol feeding and develops widespread atherosclerotic changes which progress to mature fibrous lesions morphologically indistinguishable from established human atherosclerosis. Apart from the defined genetic abnormality causing predisposition to atherosclerosis, this model has the advantage of rapid development of widespread atherosclerosis within 6 to 8 weeks following institution of cholesterol feeding.

Protocol:

LDL-R deficient mice were purchased from Jackson Laboratories. A total of 20 mice were entered into the study at 22 weeks of age, and 15 mice completed the study. The length of the study was 8 weeks. The mice were maintained on a 12 hour dark/12 hour light cycle with free access to food and water, and were fed a specified diet as follows. A control group comprised of 5 animals, all of which completed the study, received a normal diet. The high cholesterol group comprising 15 animals, of which 10 completed the study, were fed a diet containing 1.25% cholesterol, 7.5% cocoa butter, 7.5% casein, and 0.5% sodium cholate. To ensure proper food intake, food consumption and animal weight were monitored on a weekly basis. In previous experiments, it was demonstrated that 8 weeks of feeding with the high cholesterol diet results in substantial atherosclerosis development, particularly in the aortic arch and the descending thoracic aorta.

Treatment:

Ten of the animals fed the high cholesterol diet were selected at random to undergo a course of treatment by the preferred method of the invention. Six of the treated animals completed the study. It is to be noted that the four deaths in this group were not in arty way related to the treatment, but occurred early in the study as a result of fighting among animals which were housed together during the study. The other five animals on the high cholesterol diet underwent a course of sham treatments, and four survived the protocol.

The treatments began four weeks after initiation of the study, with each of the animals on the high cholesterol diet receiving a total of 10 treatments (2 courses of treatment of 1 injection per day for 5 days, the 2 courses of treatment separated by two days, i.e. 10 injections over a period of 12 days). Each individual treatment administered to the animals treated by the method of the present invention consisted of the collection of 10 ml of blood from genetically compatible donor animals fed on a normal diet, the blood being collected into sodium citrate anticoagulant. In order to collect each 10 ml aliquot of blood, about 1 ml of blood was extracted from each of 10 animals. The blood was extracted by cardiac puncture, with the animals being under fill xylazine/ketamine anesthesia during the blood extraction procedure, and being given T-61 immediately following extraction. The blood aliquot was transferred to a sterile, disposable, low-density polyethylene vessel for ex vivo treatment, and was then treated simultaneously with a gaseous oxygen/ozone mixture and ultraviolet light at elevated temperature using an apparatus as generally described in aforementioned U.S. Pat. No. 4,968,483 to Mueller et al.

The constitution of the gas mixture was 14.5±1.0 $\mu$g ozone/ml, with the remainder of the mixture comprising medical grade oxygen. The gas mixture was bubbled through the aliquot at a rate of 240±24 ml/min for a period of 3 minutes. The temperature of the aliquot was held steady at 42.5±1.0° C. The UV light was within the UV-C band, and included a wavelength of 253.7 nm.

After treatment by the preferred method of the present invention, 30 $\mu$l of the treated blood was re-injected intramuscularly into each animal undergoing treatment according to the present invention.

In the sham treatments, 30 $\mu$l of untreated blood was injected intramuscularly into each of the remaining five animals on the high cholesterol diet.

Assessment of Atherosclerosis:

After 8 weeks, the animals were anesthetized with zylaxine/ketamine and the heart was exposed. After nicking the vena cava to obtain blood samples, the animals were perfused via ventricular puncture, first with PBS to flush out the blood and then with 10% neutral buffered formalin for 3 minutes to fix the aorta. The thoracic aorta was dissected away from the thorax en bloc and stored in 10% formalin at 4° C. Pressure-fixed (10% formalin) aortae were removed en bloc and opened to allow a longitudinal full length inversion. The aortae were then mounted internally exposed on glass slides and stained with oil red O. The bright red staining (indicating lipid deposition) was then quantified using a computer assisted morphometric system, and expressed as a percentage of total aortic intimal surface.

Plasma Lipid and Lipoprotein Analysis:

Lipoprotein profiles were obtained by means of fast-phase liquid chromatography with a Superose 6B column. 200 μl aliquots of platelet-poor plasma from each animal were loaded onto the column and eluted with TSE buffer at a constant flow rate of 0.35 ml/min. An aliquot of 80 μl from each fraction was used for the measurement of total cholesterol minus esterified cholesterol. Total cholesterol and triglycerides in plasma samples and column fractions for 11 representative animals were measured by an enzymatic method established in the lipid research group at St. Michael's Hospital, Toronto.

Statistical Analysis:

Continuous variables are reported as mean ±SD. Differences in cholesterol levels and triglyceride levels among groups were tested by Student's t-test. Differences in atherosclerotic lesion area among groups were tested using the one-way ANOVA test in conjunction with the Bonferroni correction.

Results:

The measurement of the cholesterol levels among the different groups of animals showed that the total serum cholesterol level did not change significantly in the animals which received the normal diet, but was markedly increased in the animals receiving the high cholesterol diet. This marked increase occurred both in the sham treated group and to a lesser extent in the group which received the treatments according to the preferred method of the present invention.

The measured triglyceride levels were also higher in the animals which received the high cholesterol diet, as compared to the animals which received the normal diet. However, among the animals which received the high cholesterol diet, the increase in triglyceride levels was much greater in the sham treated group than in the group which was treated according to the preferred method of the present invention.

The measured cholesterol and triglyceride levels, and the average cholesterol and triglyceride levels for each group, are shown below in Table I.

TABLE I

| GROUP | ANIMAL | CHOLESTEROL (mM) | TRIGLYCERIDES (mM) |
|---|---|---|---|
| Treated | 1 | 12.99 | 0.305 |
| Treated | 2 | 13.19 | 0.336 |
| Treated | 3 | 16.22 | 0.348 |
| Treated | 4 | 14.87 | 0.397 |
| | Average (1–4) | 14.3 ± 1.5 | 0.35 ± 0.04 |
| Control | 6 | 4.41 | 0.341 |
| Control | 7 | 5.15 | 0.397 |
| Control | 8 | 5.73 | 0.440 |
| | Average (6–8) | 5.1 ± 0.7 | 0.39 ± 0.05 |
| HC Diet | 11 | 27.52 | 0.697 |
| HC Diet | 12 | 26.59 | 0.720 |
| HC Diet | 13 | 23.45 | 0.605 |
| HC Diet | 14 | 24.56 | 0.636 |
| | Average (11–14) | 25.5 ± 1.9 | 0.66 ± 0.05 |

In Table I, the "Treated" group of animals received the high cholesterol diet and were treated according to the preferred method of the present invention, the "Control" animals received the normal diet and no treatment, and the "HC Diet" animals received the high cholesterol diet and the sham treatment. From the above data, it is apparent that the ratio of the average cholesterol level of the HC Diet group to that of the Control group is 5.01:1 ($p=0.0000051$), whereas the ratio of the average cholesterol level of the Treated group to that of the Control group is 2.81:1 ($p=0.00010$). Therefore, the increase in the average cholesterol level of the Treated group is significantly lower than the increase in the average cholesterol level of the HC Diet group, with the ratio of the average cholesterol level of the Treated group to that of the HC Diet group being 0.56:1 ($p=0.000043$). These variations in cholesterol level occurred primarily in the LDL and VLDL fractions. In addition, it was found that there was no significant difference in the serum level of HDL cholesterol between the Treated and HC groups. Therefore, the treatment of the present invention does not bring about a reduction in serum HDL cholesterol, which is believed to be beneficial.

It is also apparent from the above data that the ratio of the average triglyceride level of the HC Diet group to that of the Control group is 1.69:1 ($p=0.00050$), whereas the ratio of the average triglyceride level of the Treated group to that of the Control group is 0.88:1 ($p=0.11$) Therefore, the increase in the average triglyceride level of the Treated group is significantly lower than the increase in the average triglyceride level of the HC Diet group, with the ratio of the average triglyceride level of the Treated group to that of the HC Diet group being 0.52.1 ($p=0.000034$).

EXAMPLE 2

Human Studies

The reduction in triglyceride levels observed in the animal studies is consistent with results obtained in two human studies, the results of which are presented below.

Human Study A

A total of 94 healthy human volunteers, of which 57 were males and 37 were females, were given a course of six treatments according to the preferred method of the present invention over a two week period. Serum triglyceride levels were measured before and after the course of treatments, and the average measurements are shown below in Table 2.

TABLE 2

| Pre-treatment triglyceride level (mg/dl) | Post-treatment triglyceride level (mg/dl) | Significance (p) |
|---|---|---|
| 146 | 134 | 0.04 |

Human Study B

A total of 49 patients from family practice were given various schedules of treatments according to the preferred method of the present invention. The treatments comprised from 5 to 40 injections per patient. Serum triglyceride levels of each patient were measured before and after the course of therapy and the average measurements are presented below in Table 3.

TABLE 3

| Pre-treatment triglyceride level (mg/dl) | Post-treatment triglyceride level (mg/dl) | Significance (p) |
|---|---|---|
| 135.4 | 121.9 | <0.05 |

From the above human studies, it can be concluded that the treatment according to the preferred method of the present invention achieves a significant reduction in total serum triglyceride levels in human subjects.

EXAMPLE 3

Animal Studies

In this study, LDL-R deficient mice were divided into groups and studied using the following protocol:

Group A (control)—fed a normal diet as in Example 1;

Group B1—fed a high cholesterol diet as described in Example 1 for 8 weeks;

Group B2—fed a high cholesterol diet as described in Example 1 for 12 weeks,

Group C1—fed a high cholesterol diet as described in Example 1 for 8 weeks, and treated by the preferred method of the present invention as described in Example 1 at 4 weeks of dietary intervention; and Group C2—fed a high cholesterol diet as described in Example 1 for 12 weeks, and treated by the preferred method of the present invention as described in Example 1 at 8 weeks of dietary intervention.

For each group of animals, atherosclerotic area was assessed at either 8 or 12 weeks according to the method described in Example 1 under the heading "Assessment of Atherosclerosis". As demonstrated by measurement of atherosclerotic area, the animals of group B (high cholesterol diet alone) exhibited substantial aortic lipid deposition, with group B1 animals having levels of $0.16\pm0.1$ at eight weeks and group B2 animals having levels of $0.17\pm0.1$ at 12 weeks of dietary intervention. In contrast, the animals of group C (high cholesterol diet with treatment according to the invention) exhibited profoundly reduced lipid deposition, with group C1 animals having levels of $0.04\pm0.03$ ($p<0.05$) at eight weeks of dietary intervention, and group C2 animals having levels of $0.04\pm0.02$ ($p<0.01$) at twelve weeks of dietary intervention.

The animals of group C also exhibited a marked reduction in xanthelasma and limb swelling as compared to animals of group B.

Total lipoprotein profiles were measured as in Example 1 by fast-phase liquid chromatography and an enzyme-linked assay. The results of this analysis showed that the animals of group B (high cholesterol diet alone) had markedly increased levels of total serum cholesterol (CHO $25.5\pm1.9$ mM and triglycerides as compared to control group A (CHO $5.1\pm0.7$ mM). This is to be contrasted with the animals of group C, which showed a significant reduction in both cholesterol (CHO $14.3\pm1.5$ mM; $p<0.01$ for B vs. C) and triglycerides as compared to the animals of group B.

Conclusions:

The treatment according to the preferred method of the present invention achieved about a forty percent reduction in total serum cholesterol and a significant reduction in triglyceride levels, and substantially inhibited the development of atherosclerosis in a mouse model of human familial hypercholesterolemia. In addition to substantially reducing the development of atherosclerosis at an early stage and inhibiting the progression of established atherosclerotic lesions, the treatment according to the preferred method of the present invention was shown to cause regression of existing atherosclerotic lesions. This can be seen for example by comparing the results for the animals of subgroups B1 and C2 in Example 2, which show that existing plaque deposits at week eight of a high cholesterol diet are reduced by about 75% when the animals are treated at week eight according to the present invention. These improvements in cardiovascular health were accompanied by improvements in the animals' general overall appearance and appetite. It is believed that the atherosclerosis inhibitory effect is at least partially due to the reduction in cholesterol and triglyceride levels. However, the retardation in progression and regression of the formation of atherosclerotic plaques is not necessarily accompanied by a reduction in serum lipid levels.

Furthermore, the treatment of the present invention is capable of not only preventing increases in serum lipid levels caused by a high cholesterol diet, but is also effective in reducing existing moderate to high lipid levels.

Although the invention has been described with reference to specific preferred embodiments, it will be appreciated that many variations may be made to the invention without departing from the spirit or scope thereof. All such modifications are intended to be included within the scope of the following claims.

What is claimed is:

1. A method of causing regression of an existing atherosclerotic lesion in a mammal with atherosclerosis, comprising:

(a) treating mammalian blood ex vivo with at least one stressor selected from the group consisting of a temperature above or below body temperature, ultraviolet light and an oxidative environment; and (b) administering the mammalian blood treated in step (a) to the mammal in an amount sufficient to achieve a regression in said existing atherosclerotic lesion in the mammal.

2. The method of claim 1, wherein the oxidative environment comprises applying an oxidizing agent to the aliquot.

3. The method of claim 2, wherein the oxidizing agent contains ozone gas, and the ozone gas is introduced into the blood aliquot in an amount which does not give rise to excessive levels of mutagenicity.

4. The method of claim 2, wherein the oxidizing agent comprises a mixture of ozone gas and medical grade oxygen, the ozone gas being contained in the mixture in a concentration of up to about 300 $\mu$g/ml.

5. The method of claim 4, wherein the ozone gas is contained in the mixture in a concentration of up to about 30 $\mu$g/ml.

6. The method of claim 1, wherein the mixture is applied to the aliquot at a flow rate of up to about 0.33 liters/min.

7. The method of claim 1, wherein the ultraviolet light comprises one or more UV-C band wavelengths.

8. The method of claim 1, wherein the temperature to which the aliquot is cooled or heated is a temperature which does not result in substantial hemolysis of the blood in the aliquot.

9. The method of claim 1, wherein the temperature stressor is applied so that the temperature of at least part of the aliquot is in the range of from about $-5°$ C. to about $55°$ C.

10. The method of claim 1, wherein the mean temperature of the blood in the aliquot is in the range of from about $37°$ C. to about $44°$ C.

11. The method of claim 1, wherein the mean temperature of the blood in the aliquot is in the range of from about $0°$ C. to about $36.5°$ C.

12. The method of claim 1, wherein the mean temperature of the blood in the aliquot is in the range of from about $10°$ C. to about $30°$ C.

13. The method of claim 1, wherein the temperature is in the range of from about $37°$ C. to about $55°$ C.

14. The method of claim 13, wherein the temperature is $42.5\pm1°$ C.

15. The method of claim 1, wherein the volume of the aliquot is up to about 400 ml.

16. The method of claim 15, wherein the volume of the aliquot is about 10 ml.

17. The method of claim 1, wherein the aliquot is subjected to the stressors for a period of up to about 60 minutes.

18. The method of claim 17, wherein the aliquot is subjected to the stressors for a period of about 3 minutes.

19. The method of claim 1, wherein the blood is administered to the mammal by a method suitable for vaccination selected from the group consisting of intra-arterial injection, intramuscular injection, intravenous injection, subcutaneous injection, intraperitoneal injection, and oral, nasal or rectal administration.

20. The method of claim 1, wherein all of the stressors are simultaneously administered to the aliquot.

21. The method of claim 1, wherein any two of the stressors are simultaneously administered to the aliquot.

22. The method of claim 1, wherein the blood treated in step (a) is provided by removing the blood from the same mammal to which the treated blood is administered in step (b).

* * * * *